United States Patent [19]

Van der Knaap

[11] Patent Number: Plant 6,870

[45] Date of Patent: Jun. 20, 1989

[54] CHRYSANTHEMUM PLANT NAMED LILAC MONEYMAKER

[75] Inventor: Jacques C. M. Van der Knaap, De Lier, Netherlands

[73] Assignee: Fides Beheer B.V., De Lier, Netherlands

[21] Appl. No.: 124,550

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Lilac Moneymaker, particularly characterized by its anemone capitulum type and flat capitulum form; lilac ray floret color, and by its lilac colored mature petaloids which form around the disc florets.

1 Drawing Sheet

1

The present invention comprises a new and distinct cultivar of Chrysanthemum, botanically known as *Chrysanthemum morifolium,* and referred to by the cultivar name Lilac Moneymaker.

Lilac Moneymaker is a spontaneous mutation of Moneymaker, disclosed in a pending application of applicant. Lilac Moneymaker was discovered by applicant in 1985 while growing in a cultivated bed of the parent cultivar Moneymaker. The new cultivar was immediately recognized due to its lilac ray floret color, as compared with the light pink ray floret color of Moneymaker.

The first act of asexual reproduction of Lilac Moneymaker was accomplsiehd when vegetative cuttings were taken following discovery in a controlled environment in De Lier, The Netherlands by a technician working under formulations established and supervised by applicant. Horticultural examination of selected units has demonstrated that the combination of characteristics as herein disclosed for Lilac Moneymaker are firmly fixed and are retained through successive generations of asexual reproduction.

Lilac Moneymaker has not been observed under all possible environmental conditions. The phenotype may vary significantly with variations in environment such as temperature, light intensity, and day length. The following observations, measurements and comparisons describe plants grown in De Lier, The Netherlands under greenhouse conditions which approximate those generally used in commercial practice.

The following traits have been repeatedly observed and are determined to be basic characteristics of Lilac Moneymaker, which in combination distinguish this Chrysanthemum as a new and distinct cultivar:

1. Flat capitulum form.
2. Anemone capitulum type.
3. Lilac ray floret color.
4. Diameter across the face of the capitulum is 45–50 mm.
5. Petaloids are formed around the disc florets, which are very similar in color to the ray floret color.

Except for color, Lilac Moneymaker is identical in all relevant characteristics to the parent cultivar Moneymaker.

The accompanying photographic drawing shows in front view typical inflorescence and foliage characteristics of Lilac Moneymaker, with colors being as true as possible with illustrations of this type.

2

In the following description, color references are made to The Royal Horticultural Society Colour Chart. The color values were determined between 11:00 a.m. and 12:00 noon in September under natural daylight at De Lier, The Netherlands.

Classification:

*Botanical.*—*Chrysanthemum morifolium,* Ramat., cv. Lilac Moneymaker.

*Commercial.*—Cut anemone spray.

INFLORESCENCE

A. Capitulum:

*Form.*—Flat.

*Type.*—Anemone.

*Diameter across face.*—45–50 mm.

B. Corolla of ray florets:

*Color (general tonality from a distance of three meters).*—Lilac.

*Color (upper surface).*—R.H.S. 62C-D changing to 75C at inner periphery of ray florets, and approximately 70C in mature center.

*Color (under surface).*—Somewhat lighter than 62C-D.

C. Corolla of disc florets:

*Color.*—Immature centers are yellow-green, with discs maturing to ray floret color near periphery, and petaloids of same color surrounding the disc florets.

D. Reproductive organs:

*Androecium.*—Present only in disc florets; numerous.

*Gynoecium.*—Present in both disc and ray florets; numerous.

PLANT

A. General Appearance:

*Height.*—90 cm.

B. Foliage:

*Color (upper surface).*—137A.

*Color (under surface).*—137B.

*Shape.*—Deeply serrated.

I claim:

1. A new and distinct cultivar of Chrysanthemum plant named Lilac Moneymaker, as described and illustrated, and parts thereof.

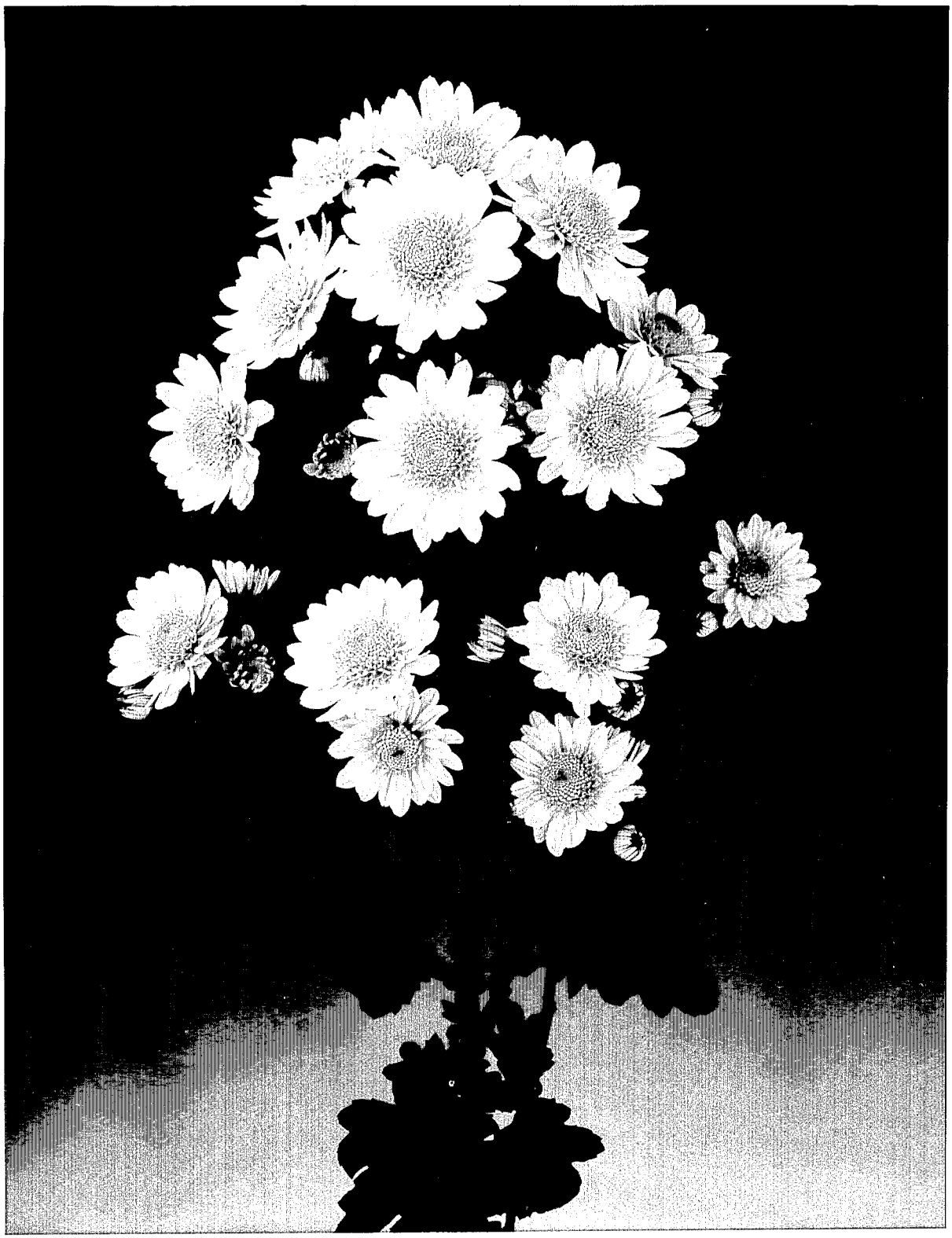

* * * * *